United States Patent [19]
Peiffer

[11] Patent Number: 4,972,949
[45] Date of Patent: Nov. 27, 1990

[54] HEMOSTATIC CLIP HOLDER FOR SMALL CLIPS

[75] Inventor: James E. Peiffer, Evergreen, Colo.

[73] Assignee: Horizon Surgical, Inc., Evergreen, Colo.

[21] Appl. No.: 532,391

[22] Filed: Jun. 4, 1990

Related U.S. Application Data

[63] Continuation-in-part of Ser. No. 412,777, Sep. 26, 1989, Pat. No. 4,936,447.

[51] Int. Cl.⁵ .............................................. B65D 85/08
[52] U.S. Cl. ..................................... 206/339; 206/340
[58] Field of Search ................................ 206/338-348; 606/142, 143, 151, 157, 158

[56] References Cited

U.S. PATENT DOCUMENTS

| | | | |
|---|---|---|---|
| 3,326,216 | 6/1967 | Wood | 606/158 |
| 3,363,628 | 1/1968 | Wood | 206/339 |
| 3,713,533 | 1/1973 | Reimels | 206/339 |
| 4,076,120 | 2/1978 | Carroll et al. | 206/339 |
| 4,146,130 | 3/1979 | Samuels et al. | 206/340 |
| 4,212,390 | 7/1980 | Raczkowski et al. | 206/341 |
| 4,294,355 | 10/1981 | Jewusiak et al. | 206/339 |
| 4,344,531 | 8/1982 | Giersch | 206/340 |
| 4,361,229 | 4/1982 | Mericle | 206/339 |
| 4,685,564 | 8/1987 | Hills et al. | 206/341 |
| 4,696,396 | 9/1987 | Samuels | 206/339 |
| 4,936,447 | 6/1990 | Peiffer | 206/339 |

*Primary Examiner*—Jimmy G. Foster
*Attorney, Agent, or Firm*—James R. Young

[57] ABSTRACT

Disclosed is a cartridge having a plurality of compartments for holding preformed hemostatic clips. Each compartment is dimensioned wide enough to hold a clip and to allow a clip applicator, which is wider than a clip, to be inserted without deforming the walls of the compartment. Each compartment has a center post or pedestal, dimensioned to be smaller than the inside dimension of a clip, that loosely supports a clip in the compartment. Centering protrusions are positioned symmetrically along the sides of the pedestal and along the walls of the compartment to help center the clip within the compartment. Each clip is held in place by two fingers that extend into the ends of the compartment and contact the clip. These fingers are made of a flexible material that allows the applicator to push the fingers aside as the applicator enters the compartment to grip a clip, and the fingers are angled and dimensioned to be long enough to remain in contact with the clip until after the applicator contacts the clip. Thus the clip is always positively retained, either by the fingers or the applicator, while in the compartment. The fingers are attached to a rim that surrounds the compartments, forming a single clip retaining component, and this component can be placed over the compartments after the clips are inseted during manufacturing. A "V" shped groove is formed into the end of each finger, which, along with the centering protrusions, holds the clip in the center of the compartment, allowing the applicator to seat the clip into the proper position within the applicator.

4 Claims, 12 Drawing Sheets

HEMOSTATIC CLIP HOLDER FOR SMALL CLIPS

BACKGROUND OF THE INVENTION

This application is a continuation-in-part of application Ser. No. 07/412,777 filed Sept. 26, 1989, now U.S. Pat. No. 4,936,447.

This invention relates to hemostatic clips used to ligate or clamp blood vessels during surgical procedures and more particularly, to a cartridge for holding hemostatic clips. Even more particularly, the invention relates to a cartridge clip holder for securely retaining a plurality of preformed hemostatic clips prior to and during the withdrawal of the clips by a clip applicator.

Hemostatic clips have been used in surgery for over 60 years. They were designed to perform two basic functions—ligation of a vessel, nerve, or fluid duct in the human body; or marking a specific surgical site, typically the periphery of a tumor, which will later show up on x-ray. The clips are permanently implanted in the body and are radiopaque. Originally hemostatic clips were formed in a "V" shape. However, when this shape is closed, it tends to push the vessel away from the clip or cut the vessel rather than clamp it. This problem was solved by a preformed hemostatic clip which resembles the shape of a horseshoe, described in U.S. Pat. Nos. 3,323,216 and 3,363,628, which is now commonly used. The horseshoe clip has two essentially parallel legs which cause an initial distal tip to tip closing action that contains the vessel within the clip to fully control the vessel before ligation.

In a typical prior art cartridge for holding the clips, a plurality of clips is press fitted over a rigid plastic center post or pedestal. The outer contour of the pedestal matches the inner horseshoe-shaped contour of the clips, however, the clip is slightly smaller than the pedestal so contact tension between the parallel legs of the clip and the pedestal prevent the clips from falling out of the cartridge during shipping and when the cartridge is inverted or dropped. This contact tension causes several problems, however.

First, it causes the process of loading the clip into the jaws of an applicator to be very inconsistent. Although the jaws of the applicators are manufactured to very precise tolerances, there are thousands of applicators in use so the jaw width opening varies significantly. A very minor jaw width variation in the applicator will cause a significant variation in the action of transferring the preformed hemostatic clip from the cartridge to the applicator jaws. Applicators with a narrow jaw opening are very difficult to force over the clip, since the clip is already in very tight contact with the pedestal and therefore not able to compress. It is possible for these applicators to scrape metal from the clip during the loading process. When the applicator has wide jaws, the clip sometimes is not securely attached within the applicator jaws after being removed from the cartridge. This may cause the hemostatic clip to slip backward within the applicator jaws and away from the intended surgical site or fall out of the applicator.

A second problem caused by the contact tension is difficulty in removing the clip from the cartridge holder. Because the clip is in contact with the pedestal, significant friction exists between the pedestal and the clip, and the cartridge must be held in place to allow removal. Either the person applying the clip must hold the cartridge in one hand and the applicator in their other hand, or the cartridge must be weighted with a significant amount of weight, before the clip and applicator can be separated from the cartridge. This causes a significant inconvenience during a surgical procedure. Because the operating room nurse responsible for loading the clips has other duties, a free hand is often not available to grasp the cartridge. Adding a base weight to the cartridge is often ineffective, since the weight may be lifted off the work surface, and since the applicator can only be used in one position with a weight under the cartridge.

A third problem with the contact tension cartridges is that the clip may scrape material from the pedestal as it is being removed. The cartridge and pedestal are usually made of plastic, and the metal clip may scrape plastic off the pedestal as the clip and applicator are removed from the cartridge. This problem is more pronounced when the clip legs have projections on their occlusive surfaces, a desirable feature for the clips. The result is that the plastic that is scraped off sticks to the clip and is left in the wound of the patient.

Yet another problem exists with prior art clip cartridge holders. In order for the applicator to fit around and hold the clip, the jaws of the applicator must be thicker than the clip. Therefore, in order for the applicator to fit into the compartment containing the clip, the compartment must be wider than the clip. If the compartment is wider than the clip, the clip can be positioned several ways within the compartment and may not be centered in the compartment when the applicator is inserted, so the clip may not be transferred accurately to the center of the jaws of the applicator. A clip which is incorrectly seated into the jaws of an applicator will yield erratic clip closure results. In addition, if the applicator is subject to jarring, the clip may fall out of the applicator jaws into the wound.

Many others have attempted to solve these problems. Reimels U.S. Pat. No. 3,713,533 issued Jan. 30, 1973 held "V" shaped clips in place by placing the legs of the clips under a lip of the cartridge rather than using contact tension with the pedestal. This cartridge was effective, but only for the "V" shaped clips—it will not work with the parallel legs of the preformed horseshoe-shaped clip.

In Carroll, et al. U.S. Pat. No. 4,076,120 issued Feb. 28, 1978, the clip compartment is built with the same width as the clip, to keep the clip centered, and a space is cut in the walls of the compartments to allow the applicator to force the compartment walls apart as the applicator is being inserted into the compartment to pick up the clip. This requires significant force to insert and remove the applicator, since the walls would attempt to hold the applicator in the compartment slot, thus two hands or a weighted base would be required to use this device.

In Samuels, et al. U.S. Pat. No. 4,146,130 issued Mar. 27, 1979, "V" shaped clips are held in place by the legs of the clips contacting the side walls of the cartridge. This device is somewhat similar to the Reimels device described above, however, in this device, the clip shape is changed from a "V" to a horseshoe by the pressure of the applicator as it is inserted over the clip. The pressure required to form the clip may cause the clip to embed itself into the pedestal and remove plastic as the clip is removed. If the clip embeds, it will be difficult to remove, thus two hands or a weighted base will be required. Also, the process of reforming the clip may scrape metal from the sides of the clip and deposit this metal near the end of the clip. The metal thus deposited may have sharp edges and be very loosely attached, so this sharp-edged metal may be dropped into the patient's wound.

The device of Jewusiak, et al. U.S. Pat. No. 4,294,355 issued Oct. 13, 1981, is designed for plastic clips having a snap closure. In one embodiment, a transparent film covers the clips. This film is perforated or embossed to form a longitudinal line of weakness along the centerline of the clips, and to form crossing lines between each clip. As the applicator is inserted into a clip compartment, it ruptures the film so the clip can be removed. In other embodiments, the clip is held in place by springs mounted to the sides or bottom of the cartridge. In all embodiments of this device, the center rail has a step that is adapted specifically to hold a particular type of plastic hemostatic clip. Also, this device does not address the problem of centering the clips within the clip compartments. Because the film would be perforated before the applicator contacts the clip, the device might not be suitable for use in any position other than horizontal.

A film or tape covering for the clips is also present in U.S. Pat. No. 4,146,130, described above. A later patent, U.S. Pat. No. 4,696,396 by this same inventor, describes a problem with this tape. According to this second patent the tape described in the first patent may stick to the clip when the clip is being removed. Another problem with tape is that the tape obscures the compartments making it more difficult to detect an empty compartment.

The device of Mericle U.S. Pat. No. 4,361,229 issued Nov. 30, 1982 is designed for a specific type of plastic hemostatic clip that has bosses on both sides of the clip legs. Fingers on the side of the cartridge engage the bosses until the applicator pushes them out of the way. Since the bosses are pushed entirely out of the way by the applicator before the applicator engages the clip, this device may not be suitable for use in any position other than horizontal. Also, in order to push the fingers out of the way, the clip is partially closed and must spring back into position after the fingers have passed by the bosses. This may cause a problem with the delicate hinge of plastic clips, and would not work with metal clips that have only a very small amount of springiness.

The device of Samuels U.S. Pat. No. 4,696,396 issued Sept. 29, 1987 has protrusions, or channel members, extending into the clip compartment from the side walls of the compartment. These channel members hold the clip in place, however, they simply change the friction point from the pedestal to the side walls, so the clip is still held in place by friction with the cartridge. Thus all the problems associated with a friction fit still apply to this device. This device may also have problems with manufacturing tolerance since neither the clip nor the channel members can be adjusted as the clips are inserted into the cartridge, therefore neither a tight fit nor a loose fit can be accommodated.

It is thus apparent that there is a need in the art for an improved system for transporting and supplying preformed hemostatic clips. There is also a need in the art for such a system that allows a preformed clip to be inserted into an applicator using only one hand. There is another need for a system wherein the preformed clip does not bind on the cartridge as it is being removed. Another need is for a system that keeps the preformed clips centered within each clip compartment in a clip cartridge. Another need is for a system that allows the preformed clip to compress as the applicator is placed over the clip. Still another need is for a system that allows the cartridge to be positioned at any angle, with respect to horizontal, while retaining the preformed clips before and during removal.

SUMMARY OF THE INVENTION

It is an object of the present invention to provide an improved system for supplying preformed hemostatic clips.

It is another object of the invention to provide an improved cartridge for preformed hemostatic clips in which the clips are not secured to a cartridge pedestal or to a cartridge side wall.

Another object of the invention is to provide a system where the preformed clips are individually removable with a minimal amount of effort during insertion of the applicator and removal of the applicator and clip from the cartridge.

Another object of the invention is to provide a cartridge for holding preformed hemostatic clips that is relatively economical to produce.

Still another object is to provide an improved cartridge which holds the preformed clips in place without friction between the clip and the pedestal or between the clip and the cartridge side walls.

Still another object is to provide an improved cartridge wherein the preformed clip does not bind on the pedestal during removal and therefore does not ablate cartridge material during such removal.

Still another object is to provide such a cartridge that allows the insertion of a preformed clip into an applicator and the removal of the clip from the cartridge with one hand.

Another object is to provide a cartridge what allows the preformed clip to compress in order to custom fit to the applicator as the applicator is pushed over the clip.

A further object of the invention is to provide an improved cartridge that centers the preformed clip within the chamber holding the clip.

A further object is to provide such a cartridge that has clip centering protrusions in the compartments of the cartridge.

A still further object is to provide an improved cartridge system having retaining fingers that hold the preformed clips in the cartridge.

A further object is to provide a cartridge wherein each retaining finger has a groove in its end to assist in centering the preformed clip within a compartment.

A further object is to provide a cartridge wherein the retaining fingers swing away from the preformed clip as the applicator is pushed over the clip whereby the clip does not have to compress and spring back as the fingers swing away.

A further object is to provide a cartridge wherein the retaining fingers swing below the applicator during insertion of the preformed clip into the applicator and help push the applicator back out of the chamber thus easing the removal of the preformed clip and applicator.

A further object is to provide a cartridge wherein the applicator contacts the preformed clip before the retaining fingers swing away from the clip during insertion of the clip into the applicator whereby the preformed clip is always retained allowing the cartridge to be positioned at any angle including upside down.

A further object is to provide a cartridge wherein the retaining fingers are formed as a single unit and placed over the preformed clips after the clips have been placed in the cartridge.

A still further object of the invention is to provide an improved cartridge that will perform correctly even after being subjected to a wide temperature range.

Yet another object is to provide a cartridge that can be used with preformed clips having either a raised occlusive surface or a recessed occlusive surface.

Still another object is to provide such a cartridge wherein the base is made of a light colored material and the retaining fingers are made of a dark colored material to facilitate detection of empty clip compartments.

The above and other objects are accomplished with a cartridge having a plurality of compartments, each of which will hold one hemostatic clip. Each compartment is dimensioned wide enough to hold the clip and to allow a clip applicator, which is wider than a clip, to be inserted without deforming the walls of the compartment. Each compartment has a pedestal, dimensioned to be smaller than the inside dimension of a clip, that loosely supports a clip in the compartment. Centering protrusions are positioned symmetrically along the sides of the pedestal and along the walls of the compartment to help center the clip within the compartment.

Each clip is held in place by two fingers that extend into the ends of the compartment at a downward angle to and contact the clip. These fingers are made of a flexible material that allows the applicator to push the fingers aside as the applicator enters the compartment to grip a clip. The fingers are dimensioned to be long enough to remain in contact with the clip until after the applicator contacts the clip. The fingers also extend at a downward angle toward the clip so that they will be pushed out of the way of the applicator and will not be caught between the applicator and the clip. Thus the clip is always positively retained, either by the fingers or the applicator, while in the compartment. This allows the cartridge to be held in any position while a clip is being removed.

The fingers are attached to a rim that surrounds the compartments, forming a single clip retaining component, and this component can be placed over the compartments after the clips are inserted during manufacturing. A "V" shaped groove is formed into the end of each finger. This groove, and the centering protrusions, hold the clip in the center of the compartment, allowing the applicator to seat the clip into the proper position within the applicator.

Because the pedestal is smaller that the clip, and the clip is held in place by the fingers, only a small amount of force is required to place the applicator over a clip, thus a clip can be placed into an applicator with one hand. This smaller pedestal allows the clip to compress slightly in order to custom fit to the applicator as the applicator is pushed over the clip. Also, the smaller pedestal significantly reduces the likelihood of removing material from the pedestal as the clip is removed from the compartment.

A shelf at the base of the pedestal forms a stop for the applicator after the applicator has been completely placed over the clip. For very small clips, where the applicator is proportionally larger with respect to the clips then an equivalent applicator for larger clips, the base of the pedestal is not large enough to form such a stop. Furthermore, for small clips, the fingers are longer than equivalent fingers on larger clips. Therefore, the base for smaller clips is formed having a groove and a recessed section located outside the base of the pedestal.

As the applicator is placed over the small clip, the fingers are forced downward and the ends of the fingers come to rest in the groove. The groove prevents the finger from sliding outward, and the applicator presses the finger down over the recessed portion. The thickness of the finger combined with the recessed outer portion of the pedestal, combined to form a stop for the applicator as it is being pressed over the smaller clip.

BRIEF DESCRIPTION OF THE DRAWINGS

The above and other objects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

In general, the present invention comprises a cartridge having a plurality of compartments, each of which is suitable for holding a preformed hemostatic clip. Each compartment has a pedestal, dimensioned to be smaller than the inside dimension of a hemostatic clip, which loosely supports a clip in the compartment. Each clip is held in place by two fingers that extend from a rim into the compartment and contact the clip. These fingers are made of a flexible material that allows an applicator to push the fingers aside as the applicator enters the compartment to grip a clip. Because of the length and angle of the fingers, they remain in contact with the clip until after the applicator contacts the clip. A groove, formed into the end of each finger, and centering protrusions, positioned symmetrically along the sides of the pedestal and along the walls of the compartment, hold the clip in the center of the compartment. This allows the applicator to seat the clip into the proper position within the applicator.

Only a small amount of force is required to place the applicator over a clip, because the pedestal is smaller than the clip, and the clip is held in place by the fingers. Thus a clip can be placed into an applicator with one hand. This smaller pedestal allows the clip to compress slightly in order to custom fit to the applicator as the applicator is pushed over the clip. Also, the smaller pedestal significantly reduces the likelihood of removing material from the pedestal as the clip is removed from the compartment.

Figure 1:
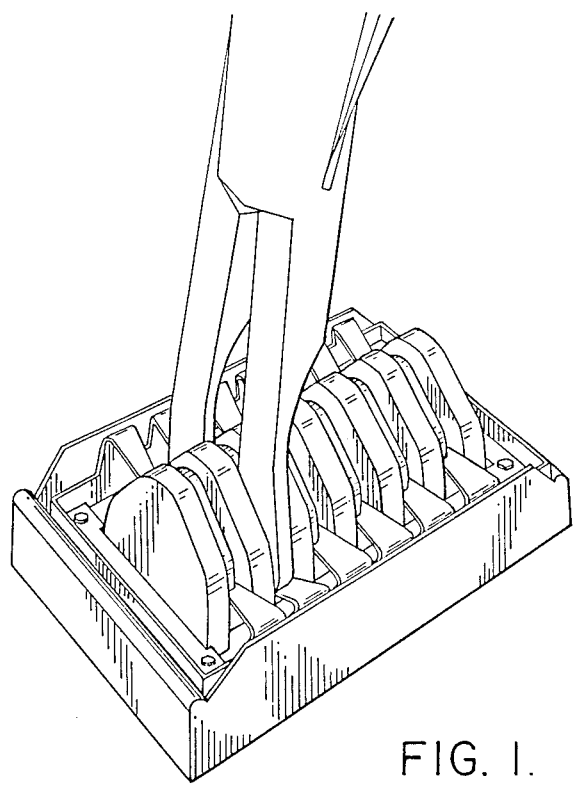
FIG. 1 shows a perspective view of the cartridge of the present invention with an applicator inserted therein.

FIG. 1 shows a perspective view of the cartridge, and shows an applicator positioned over a clip in one of the compartments. Referring now to FIG. 1, a cartridge 10 is shown having a base component 12. Formed into the base component 12 are a plurality of clip compartments 14, separated by walls 26. Each of the compartments 14 will hold one hemostatic clip (not shown in this figure). Each clip compartment 14 is wide enough to allow an applicator 16 to be inserted into the compartment 14, without deforming the walls 26 of the compartment 14, to introduce the clip contained in the compartment 14 into the jaws 18 of the applicator 16. The clips are held in the cartridge 10 by a plurality of clip retaining fingers 20, which are attached to a rim 22. The cartridge 10 has two fingers 20 for each compartment 14, one located on each side of the compartment.

In operation, the applicator 16 is positioned over a compartment 14 and pressed downward into one of the compartments 14. As the applicator moves downward, the fingers 20 in the compartment 14 are deformed down into the compartment 14 and away from the legs of the clip (not shown). This is illustrated in FIG. 1 by the pair of clip retaining fingers 24 being bent downward by the applicator jaws 18. The fingers 24 are pushed out of the way of the applicator 16 and away from the clip as the applicator jaws 18 are fully inserted into the compartment 14.

Figure 2A:
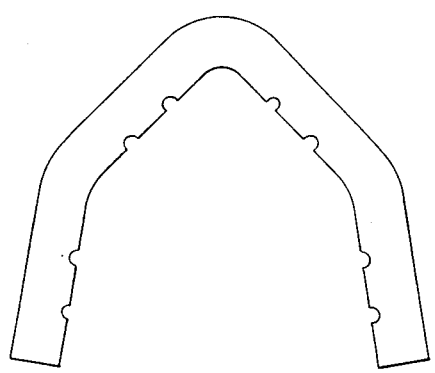
FIG. 2A is a side view of a clip used with the present invention.
Figure 2B:
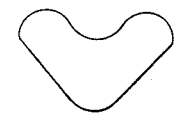
FIG. 2B is an end view of a clip used with the present invention.

FIGS. 2A and 2B show a side view and an end view, respectively, of a prior art clip, described generally in Wood U.S. Pat. No. 3,363,628 issued Jan. 16, 1968, which is suitable for use with the present invention. Other clips are also suitable for use with the invention, for example plastic clips having a retaining hook or snap closure will also work with the present invention. Referring now to FIG. 2A, a horseshoe-shaped clip 30 is shown. The horseshoe-shape is formed by a bend 36 in each leg of the clip 30, although the angle of the legs of the clip varies with different prior art clips. A plurality of slots 32 in the occlusive surface 34 of the clip 30 help to hold the clip 30 in position on a vessel, once the clip 30 has been clamped into place, thus the slots 32 are important to the operation of the clip 30. As will be shown later, the pedestal of the cartridge of the present invention is designed so that the slots 32 do not scrape away material as the clip 30 is being removed from the clip compartment by the applicator.

FIG. 2B shows an end view of the clip, and illustrates the shape of the clip. The occlusive surface 34 has a pair of rounded sections separated by a groove. The outside edge of the clip is generally triangular in shape, having a peak 38 to fit in a groove of the applicator.

Figure 3:
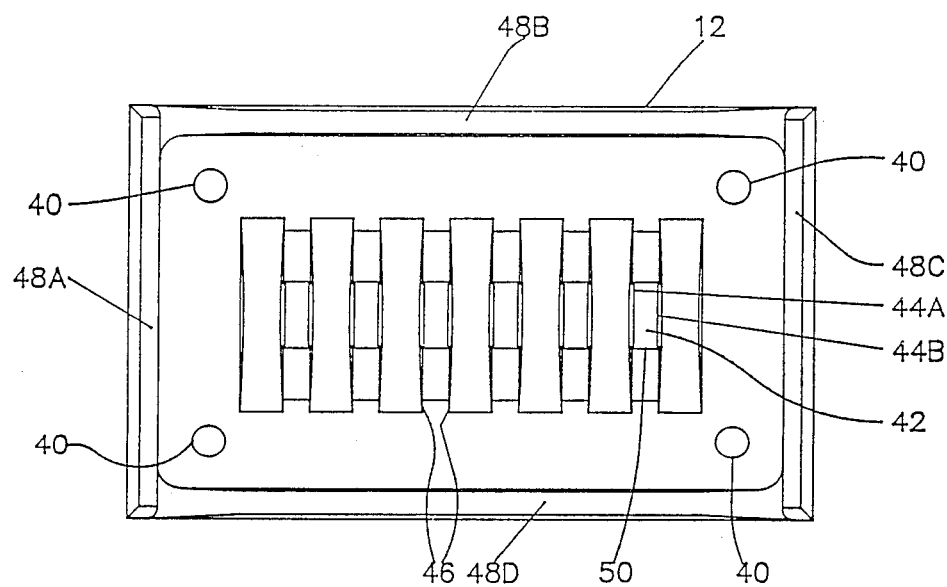
FIG. 3 is a top view of the base component of the present invention.

FIG. 3 shows a top view of the base component of the present invention. Referring now to FIG. 3 the compartments 14 in the base component 12 are illustrated. The base component 12 is generally rectangular in shape, and is typically molded from rigid material that can be sterilized for surgical use, for example material such as ABS (Acrylonitrile-butadiene-styrene copolymers). It is typically colored using a light color to facilitate detecting empty compartments in an operating room environment. Alignment and permanent assembly posts 40 are positioned on the base component 12, and generally molded into the base, to insure alignment of the rim 22, as the rim 22 is placed over the base component 12. A centering slot 42 within each compartment 14 contains a pair of centering protrusions 44A and 44B to help center the clip (not shown) within the compartment 14. The protrusions 44A and 44B are attached to the side walls 46 of the compartment 14 and also to a pedestal 50. The outer contour of the pedestal 50 is the same as the inner contour of the clip 30 (FIG. 2), however, the pedestal 50 is smaller in size than the inner contour of the clip 30.

Horizontal support members 48A and 48C are located at both ends of the base component 12, and serve to structurally strengthen the base component 12. Side walls 48B and 48D strengthen the base component 12, and serve to protect the fingers from being prematurely depressed. All four walls, 48A, 48B, 48C, and 48D, create a pocket into which the clip retainer 60 (FIG. 5) is placed.

Figure 4:
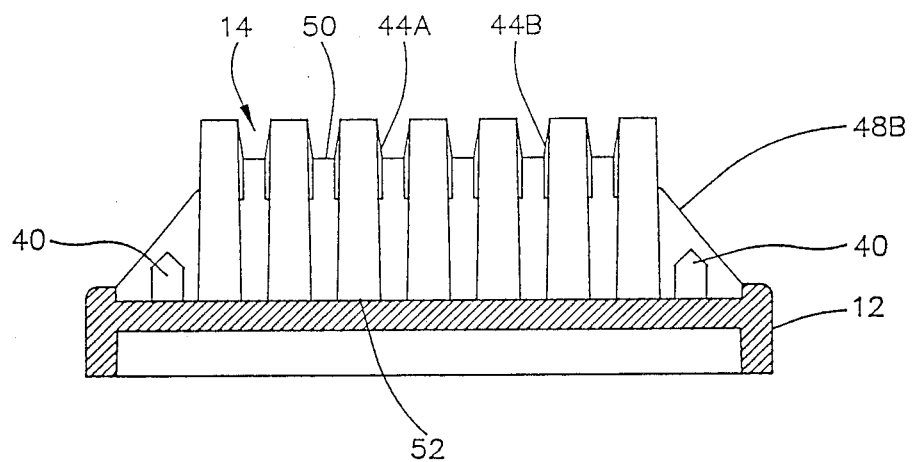
FIG. 4 is a side view of the base component.

FIG. 4 shows a side view of the base component 12. Referring now to FIG. 4, the base component 12 is shown, having the side wall 48B on the side of the base component 12. The pedestal 50 is shown extending down through the clip compartment 14 to the bottom 52 of the base component 12. The alignment posts 40 are shown with a pointed top, which helps align the rim as it is placed over the base component 12 and lowered onto the alignment posts 40. This figure also shows that the centering protrusions 44A and 44B extend down into the compartment 14 below the top of the pedestal 50.

Figure 5:
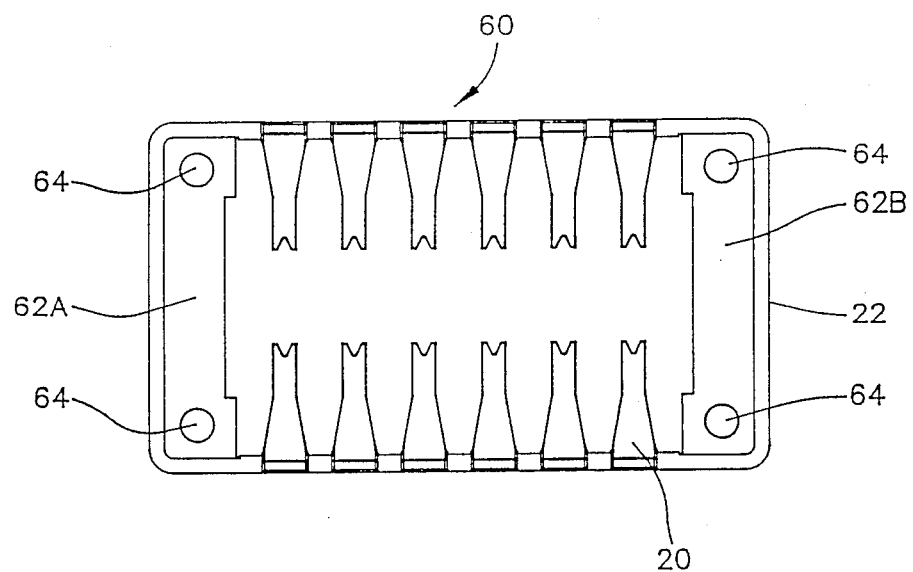
FIG. 5 is a top view of the clip retaining component of the present invention.

FIG. 5 shows a top view of the clip retaining component of the invention. Referring now to FIG. 5, the clip retaining component 60 has a rim 22 (also shown in FIG. 1) and a plurality of fingers 20 (also shown in FIG. 1) attached to the rim 22. The clip retaining component is typically molded from flexible material that can be sterilized for surgical use, for example material such as Nylon 101. It is typically colored with a dark color to contrast with the light colored base component, and may be colored differently for different sized clips. The rim 22 has one pair of fingers 20 for each compartment 14 in the base component 12 (FIG. 1). A pair of horizontal support members 62A and 62B provide structural support for the rim 22 so that it does not bend easily during the manufacturing process. Four holes 64 are of a size, shape and location to allow them to mate with the alignment posts 40 of the base component 12 (see FIG. 3). During the assembly process the clips 30 are placed in the compartments 14, and then the clip retaining component 60 is placed over the clips 30, and over the alignment posts 40. The clip retaining component 60 is then permanently attached to the base component 12 by reforming the alignments posts 40 to make their ends larger than the holes 64. This reforming may be done by ultrasound staking, heat staking, or other means.

The cartridge 10 is economical to produce, because the cartridge 10 has only two parts—the base component 12 and the clip retaining component 60, and because of the alignment posts 40 and the holes 64 provide for rapid and accurate alignment of the clip retaining component 60 over the base component 12. Also, the device will work over a wide temperature range because the clips are held in place by the fingers, and do not require a friction fit with any part of the cartridge.

Figure 6:
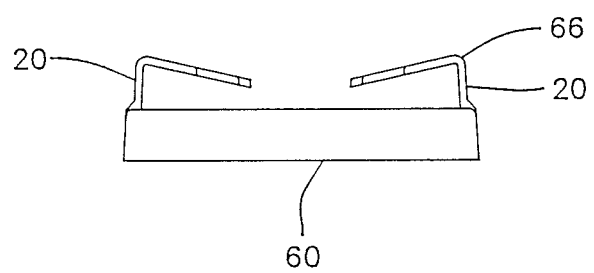
FIG. 6 is a end view of the clip retainer.

FIG. 6 shows an end view of the clip retaining component 60. This figure illustrates the bend 66 in the clip retention fingers 20 which allows the fingers 20 to slope downward toward the clips 30 (not shown). The downward slope ensures that the finger 20 will swing away from the clip as they are being depressed by the applicator. This insures that the clip is not partially compressed prior to seating in the applicator jaws. The downward slope also ensures that the applicator will meet minimal resistance from the fingers 20 as it is placed over the clip 30. It also allows the fingers 20 to contact the clip below the bend 36 in the clip (FIG. 2A), which allows the fingers to release more easily.

The fingers 20 could also be designed to be perpendicular to the rim 22. This could be satisfactory so long as the fingers do not get caught between the applicator jaws and the preformed clip. If the fingers do get between the clip and the jaws, the clip will be compressed and may not spring back completely into the jaws.

Figure 7:
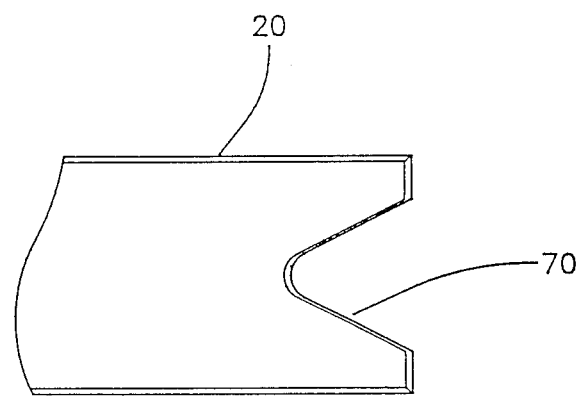
FIG. 7 is a top view of a clip retaining component finger.

FIG. 7 shows a larger view of the tip of the fingers 20. Referring now to FIG. 7, the tip of the finger 20 contains a groove 70 which is designed to fit over the triangular peak 38 (shown in FIG. 2B) of the clip 30. By fitting over the peak 38, the groove 70 centers the side legs of the clip in a fixed position within the compartment 14.

Figure 8:
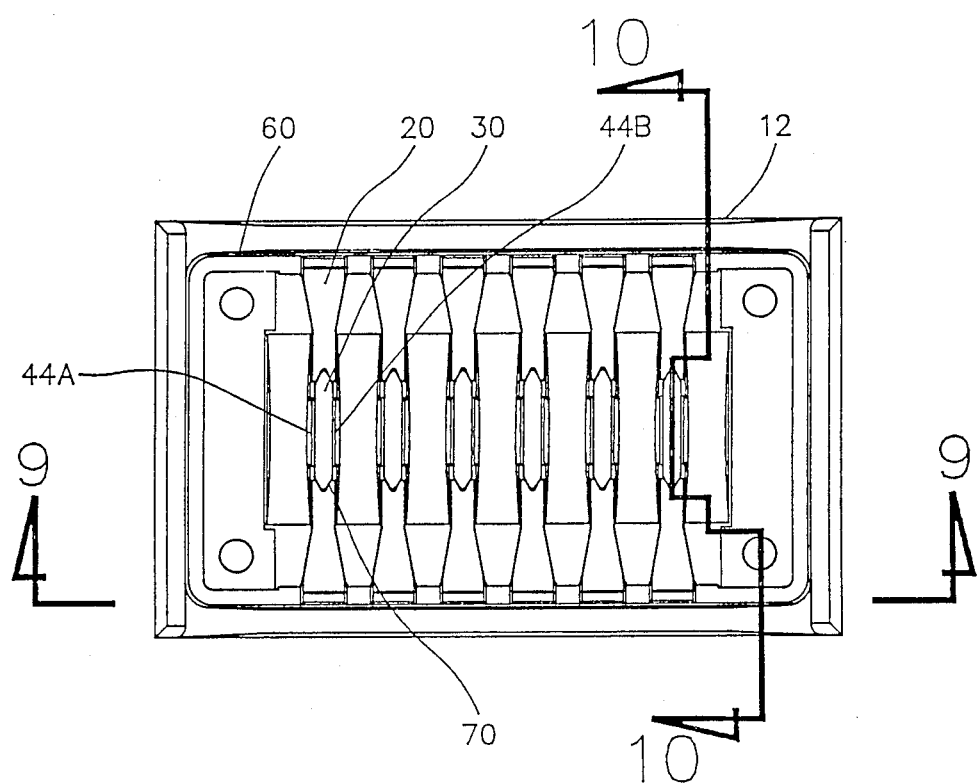
FIG. 8 is a top view of the cartridge showing clips contained therein.
Figure 9:
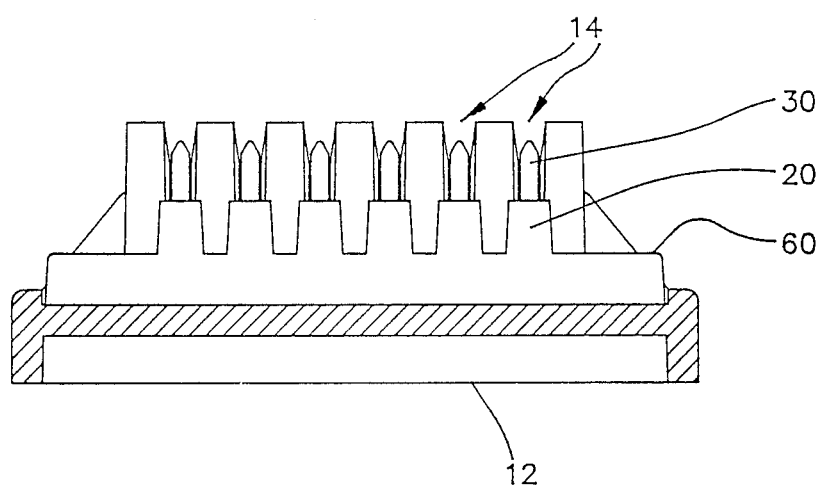
FIG. 9 is a side view of the cartridge showing clips therein.

FIG. 8 shows a top view of the cartridge 10, and FIG. 9 shows a side sectional view taken through the line B—B of FIG. 8. Referring now to FIGS. 8 and 9, the base 12 is shown with compartments 14, each of which contains a hemostatic clip 30. the clip retaining component 60 is attached to the base 12, and each of the fingers 20 are positioned over a clip 30. FIG. 8 illustrates the groove 70 in each of the fingers 20 mating with the clip 30 to hold the clip in place. The combination of the groove 70 and the protrusions 44A and 44B hold the clip 30 in the center of the compartment 14. The centering of the clip 30 within the compartment 14 significantly enhances the ability of the applicator to properly seat a clip within the jaws of the applicator.

Figure 10:
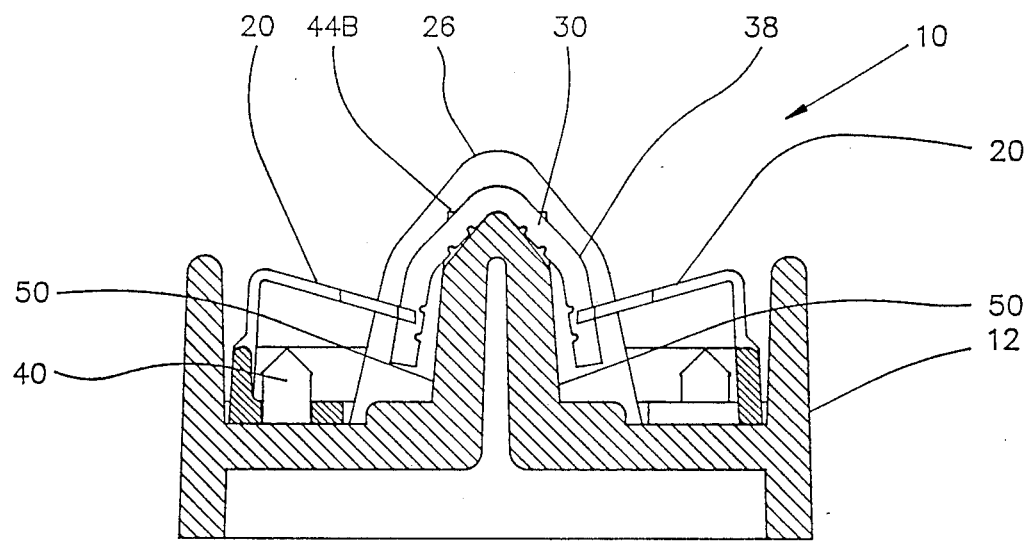
FIG. 10 is a section end view of the cartridge, taken through the line A—A of FIG. 8, showing a clip being retained by the fingers.

FIG. 10 shows an end section view of the cartridge 10, taken through the line A—A of FIG. 8. Referring now to FIG. 10, The base component 12 is shown having the pedestal 50 formed therein, and formed to be smaller than the clip 30. Because the pedestal 50 is smaller than the clip 30, there is no friction contact between the clip 30 and the pedestal 50. The lack of friction allows the clip to be removed more easily than in prior art devices, and prevents the clip 30 from scraping material from the pedestal as the clip is removed. In addition, since there is space between the clip 30 and the pedestal 50, the clip can deform inward as the applicator is placed over the clip, thus allowing the clip to custom fit to the shape of the applicator. This space also allows the cartridge to be used with clips having either a raised occlusive surface or a recessed occlusive surface.

This figure also shows that the downward slope of the fingers 20 allows the fingers 20 to contact the clip 30 at a point on the leg of the clip 30 below the bend 38. This allows the finger 20 to move smoothly away from the clip 30 as the applicator is applied. Because the fingers 20 contact the distal legs of the clip 30, they center these legs within the compartment 14, while the protrusions 44A (not shown) and 44B center the top of the clip 30. In this manner, the clip 30 remains fully centered within the compartment 14.

Figure 11:
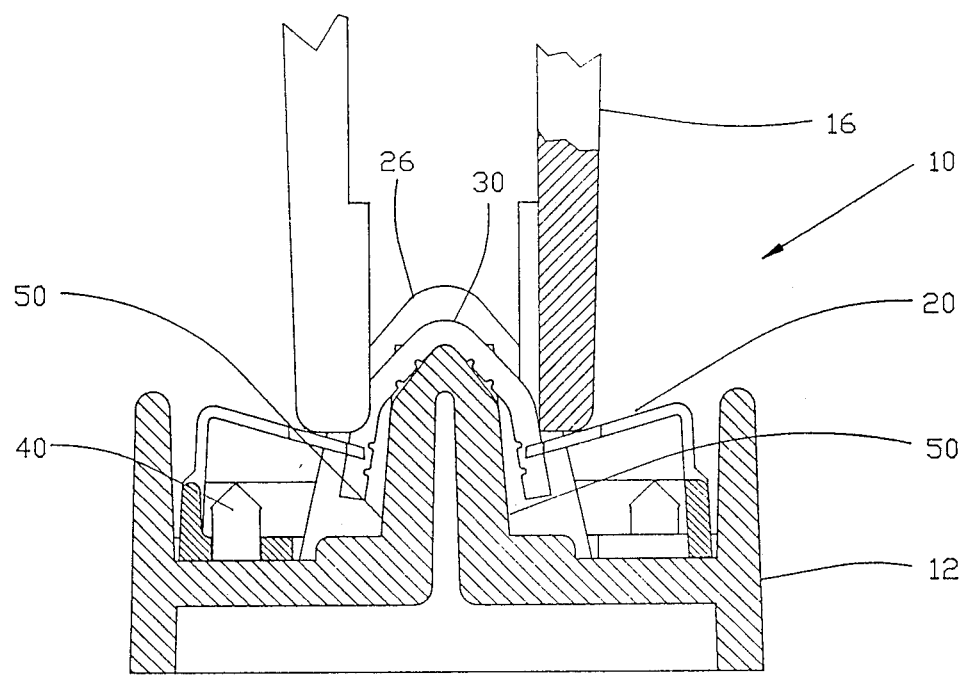
FIG. 11 is a section end view of the cartridge showing an applicator positioned over a clip.

FIG. 11 shows an end section view of the cartridge 10, with an applicator being placed over a clip. Referring now to FIG. 11, as the applicator 16 is being placed over the clip 30 it contacts the clip 30 before the fingers 20 are pushed out of the way. This provides that the clip 30 is always in positive contact with either the fingers 20 or the applicator 16, thus the cartridge 10 can be placed in any position, even upside down, without the clip falling out of the cartridge during removal. This feature allows the cartridge 10 to be held, in any position, and the cartridge brought to the applicator, as well as the conventional method of placing the cartridge o a flat surface and bringing the applicator to the cartridge.

Figure 12:
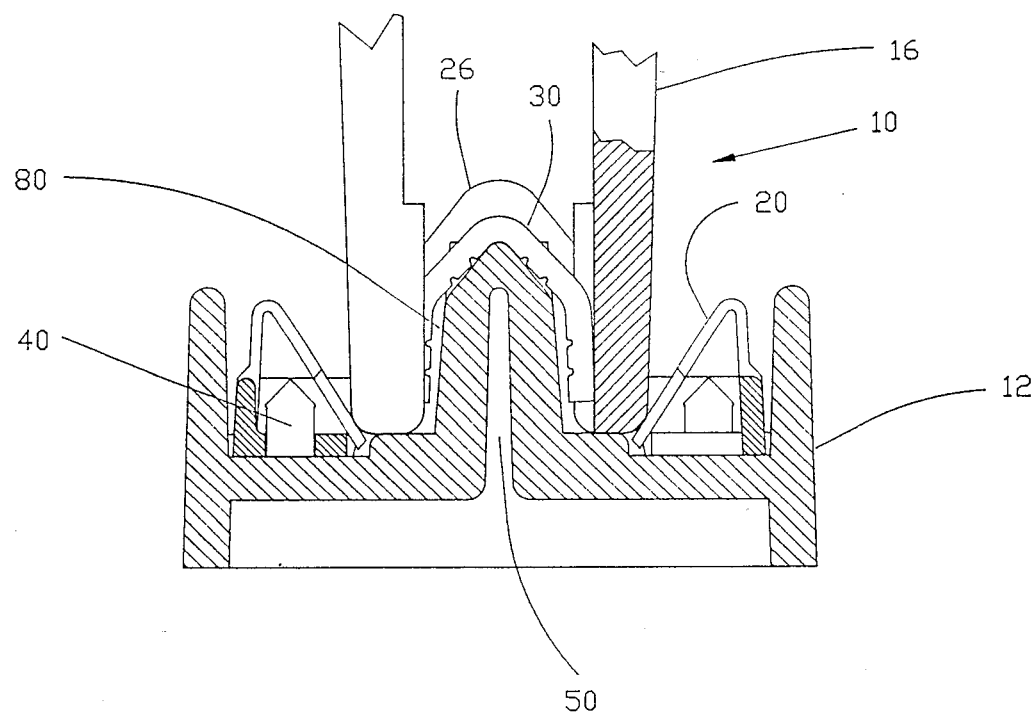
FIG. 12 is a section end view of the cartridge showing an applicator fully in place over a clip.

FIG. 12 shows an end section view of the cartridge 10, with an applicator fully in place over a clip. Referring now to FIG. 12, the applicator 16 is shown fully in place over the clip 30. The fingers 20 have been pushed down and away from the clip 30, thus allowing the clip 30 to easily be removed from the cartridge 10. Because the pedestal 50 is smaller than the clip 30, a gap 80 remains between the clip 30 and the pedestal 50, even with the applicator 16 fully in place.

While the fingers 20 are flexed out of the way of the clip 30 and applicator 16, they still contact the end of the applicator 16, and they push against the end of the applicator to assist the applicator as it is being removed from the cartridge.

The combination of the narrow pedestal 50 and the fingers 20 permit the preformed hemostatic clip 30 to be compressed and custom fitted to any extremes of manufacturing tolerance of the applicator 16. The downward force required by the operator to load the clip 30 into the applicator 16 is reduced dramatically from prior art devices designed for use with preformed hemostatic clips. The loading action is very smooth and precise and the clip locks firmly within the jaws of the applicator. The groove 70 in the end of the fingers 20, along with the protrusions 44A and 44B insure that the clip 30 is centered within the compartment 14, thus insuring proper seating of the clip 30 within the applicator 16.

The flexible clip retainer fingers 20 move freely out of the way of the applicator 16 during the process of transferring the clip from the cartridge into the jaws of the applicator, thus insuring a smooth release of the applicator from the cartridge with the use of only one hand and without the use of any additional devices, such as a base weight. Since the fingers are resilient and attempt to return to their relaxed state, they act as a spring to help eject the applicator 16 from the cartridge 10.

Figure 13:
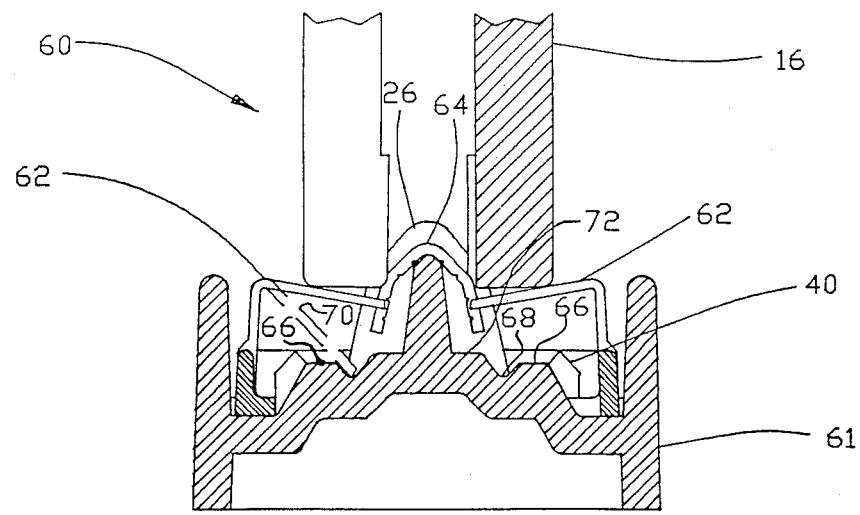
FIG. 13 shows a section end view of a cartridge for very small clips, with an applicator positioned over a clip.

FIG. 13 shows an end section view of a cartridge 60 designed for use with very small clips. Referring now to FIG. 13, the view shows an applicator being placed over a very small clip 64. As the applicator 16 is being placed over the clip 64 it contacts the clip 64 before the fingers 62 are pushed out of the way. Fingers 64 are relatively longer that the fingers 20 used with larger clips. The ends of the fingers 62 are pushed into a recess 68 of the base 61 of the cartridge, as shown by the dotted lines 70. The recess 68 traps the ends of the fingers, and allows the finger to fold over and fit on top of the protrusion 66. The protrusion 66 is lower than the pedestal base 72. The difference in height between the protrusion 66 and the pedestal base 72 is approximately the thickness of the finger 62. Therefore, as the finger 62 folds over the protrusion 66, the resulting height is the same as the height of the pedestal base 72. Thus, the base of the pedestal 72, the protrusion 66 and finger 62 are at a height to allow them to form a stop for the applicator 16.

Figure 14:
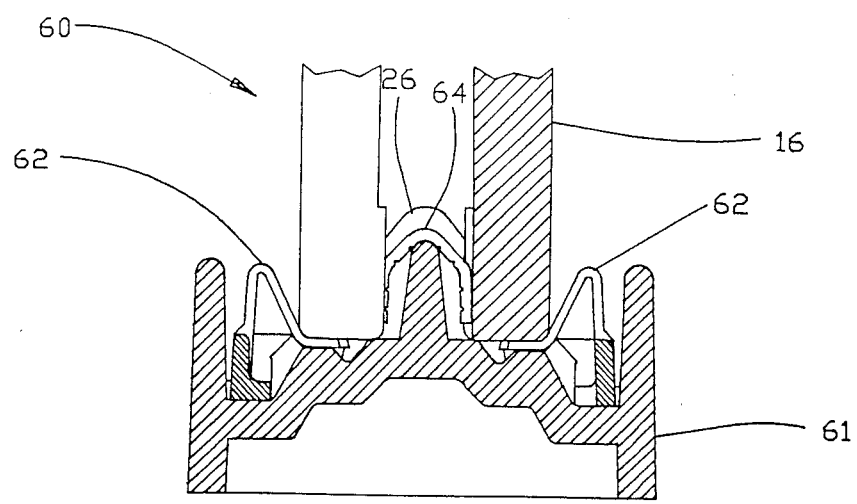
FIG. 14 is a section end view of the cartridge for smaller clips showing an applicator fully in place over a clip.

FIG. 14 shows an end section view of the cartridge 60, with an applicator fully in place over a clip 64. Referring now to FIG. 14, the fingers 62 have been pushed down and away from the clip 64, into the recess 68 and conformed over the protrusion 66, to form a firm stop for the applicator 16, thus allowing the clip 64 to easily be removed from the cartridge 60. While the fingers 62 are flexed out of the way of the clip 64 and applicator 16, they still contact the end of the applicator 16, and they push against the end of the applicator to assist the applicator as it is being removed from the cartridge.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the spirit and scope of the present invention. The disclosures and the description herein are intended to be illustrative and are not in any sense limiting of the invention, more preferably defined in scope by the following claims.

What is claimed is:

1. A cartridge for storing and singly dispensing hemostatic clips which are preformed into a shape suitable for engagement by a clip applicator, said cartridge comprising:
    a base component having a plurality of clip compartments each of said compartments comprising
        a pair of compartment side walls for containing a clip,
        a pedestal for loosely supporting said clip, and
        a base formed at a bottom of said pedestal comprising
            a surface formed essentially at a right angle to a direction of travel of said applicator, and
            a protrusion located adjacent said surface and extending upward from said base component to a level below said surface; and
    retaining means for retaining said clip in each of said compartments comprising a pair of fingers extending into each of said clip compartments wherein each of said fingers has a contacting end that contacts said clip.

2. The cartridge of claim 1 further comprising a groove formed between said surface and said protrusion.

3. The cartridge of claim 2 wherein said level below said surface is essentially equal to a thickness of one of said fingers.

4. The cartridge of claim 1 wherein said level below said surface is essentially equal to a thickness of one of said fingers.

* * * * *